(12) United States Patent
De Sapio et al.

(10) Patent No.: US 10,130,311 B1
(45) Date of Patent: Nov. 20, 2018

(54) IN-HOME PATIENT-FOCUSED REHABILITATION SYSTEM

(71) Applicant: HRL Laboratories, LLC, Malibu, CA (US)

(72) Inventors: Vincent De Sapio, Westlake Village, CA (US); Suhas E. Chelian, San Jose, CA (US); Rajan Bhattacharyya, Sherman Oaks, CA (US); Matthew E. Phillips, Calabasas, CA (US); Matthias Ziegler, Oakton, VA (US); David W. Payton, Calabasas, VA (US)

(73) Assignee: HRL Laboratories, LLC, Malibu, CA (US)

( * ) Notice: Subject to any disclaimer, the term of this patent is extended or adjusted under 35 U.S.C. 154(b) by 226 days.

(21) Appl. No.: 15/158,478

(22) Filed: May 18, 2016

Related U.S. Application Data

(60) Provisional application No. 62/163,286, filed on May 18, 2015.

(51) Int. Cl.
*A61B 5/00* (2006.01)
*A63B 24/00* (2006.01)
*G09B 5/02* (2006.01)
*G09B 19/00* (2006.01)
*A61H 3/00* (2006.01)

(52) U.S. Cl.
CPC .......... *A61B 5/7455* (2013.01); *A61B 5/6803* (2013.01); *A61H 3/00* (2013.01); *A63B 24/0062* (2013.01); *A63B 24/0075* (2013.01); *G09B 5/02* (2013.01); *G09B 19/003* (2013.01); *A63B 2024/0081* (2013.01); *A63B 2225/50* (2013.01); *A63B 2225/52* (2013.01)

(58) Field of Classification Search
None
See application file for complete search history.

(56) References Cited

U.S. PATENT DOCUMENTS

| | | | |
|---|---|---|---|
| 2012/0108909 A1* | 5/2012 | Slobounov | A61B 5/1124 600/300 |
| 2013/0054264 A1* | 2/2013 | Baronov | G06F 19/3456 705/2 |
| 2013/0198625 A1* | 8/2013 | Anderson | G06F 3/016 715/701 |

(Continued)

OTHER PUBLICATIONS

Anselme, P. (2010). The uncertainty processing theory of motivation. Behavioural Brain Research, 208 (2), pp. 291-310.

(Continued)

*Primary Examiner* — Jason Yen
(74) *Attorney, Agent, or Firm* — Tope-McKay & Associates

(57) ABSTRACT

Described is a system for patient-specific rehabilitation that can be performed outside a clinic. The system monitors a patient in real-time to generate a quantitative assessment of a physical state and a motivational state of the patient using sensor data obtained from sensors. Predictions related to the patient are generated utilizing patient-specific biomechanical and neurocognitive models implemented with predictive simulations. Video feed of the patient is registered with sensor data and a set of simulation data. Rehabilitation guidance instructions are conveyed to the patient through dialog-based interactions.

17 Claims, 11 Drawing Sheets

(56) References Cited

U.S. PATENT DOCUMENTS

| | | | | |
|---|---|---|---|---|
| 2014/0276242 | A1* | 9/2014 | Chen | A61B 5/112 600/595 |
| 2014/0295392 | A1* | 10/2014 | Rock | G06F 19/3418 434/257 |
| 2015/0133820 | A1* | 5/2015 | Zohar | A61B 5/1118 600/595 |
| 2015/0148619 | A1* | 5/2015 | Berg | A61B 5/0024 600/301 |
| 2016/0045386 | A1* | 2/2016 | Sandler | A61B 5/7415 623/24 |
| 2016/0085927 | A1* | 3/2016 | Dettinger | G06Q 10/00 705/2 |

OTHER PUBLICATIONS

Axelrod, L., Fitzpatrick, G., Balaam, M., Mawson, S., Burridge, J., Ricketts, I., et al. (2011). A toolkit to explore lived experience of motivation: When words are not enough. Proceedings of the 5th International Conference on Pervasive Computing Technologies for Healthcare, pp. 32-39.

Balaam, M., Rennick Egglestone, S., Fitzpatrick, G., Rodden, T., Hughes, A., Wilkinson, A., et al. (2011). Motivating mobility: designing for lived motivation in stroke rehabilitation. Proceedings of the 2011 Conference on Human Factors in Computing Systems, pp. 3073-3082.

Berridge, K. C. (2004). Motivation concepts in behavioral neuroscience. Physiology & Behavior, 81 (2), pp. 179-209.

Brown, J. W., Reynolds, J. R., & Braver, T. S. (2007). A computational model of fractionated conflict-control mechanisms in task-switching. Cognitive Psychology, 55 (1), pp. 37-85.

Chang, C., Lange, B., Zhang, M., Koenig, S., Requejo, P., Somboon, N., et al. (2012). Towards pervasive physical rehabilitation using Microsoft Kinect. 2012 6th International Conference on Pervasive Computing Technologies for Healthcare (PervasiveHealth), pp. 159-162.

Clark, R. B., Pua, Y., McCrory, P., Bennell, K., & Hunt, M. (2010). Validity and reliability of the Nintendo Wii Balance Board for assessment of standing balance. Gait & Posture, 31 (3), pp. 307-310.

Delp, S., Anderson, F., Arnold, A., Loan, P., Habib, A., John, C., et al. (2007). OpenSim: Open-Source Software to Create and Analyze Dynamic Simulations of Movement. IEEE Transactions on Biomedical Engineering, 54 (11), pp. 1940-1950.

Edginton, K., Güler, H. O., & Berme, N. (2008). Instrumented Treadmills: Reducing the Need for Gait Labs. White Paper, Bertec Corporation, pp. 1-4.

Egglestone, S. R., Axelrod, L., Nind, T., Turk, R., Wilkinson, A., Burridge, J., et al. (2009). A design framework for a home-based stroke rehabilitation system: identifying the key components. Proceedings of the 3rd International Conference on Pervasive Computing Technologies for Healthcare, pp. 1-8.

Frank, M. J. (2011). Computational models of motivated action selection in corticostriatal circuits. Current Opinion in Neurobiology, 21 (3), pp. 381-386.

Fregly, B., Reinbolt, J., Rooney, K., Mitchell, K., & Chmielewski, T. (2007). Design of patient-specific gait modifications for knee osteoarthritis rehabilitation. IEEE Transactions on Biomedical Engineering, 54 (9), pp. 1687-1695.

Jercic, P., Astor, P., Adam, M., & Hilborn, O. (2012). A serious game using physiological interfaces for emotion regulation training in the context of financial decision-making. Proceedings of the European Conference of Information Systems, ECIS 2012, Proceedings. Paper 207.

Johnson, J. G. (2009). Embodied cognition of movement decisions: a computational modeling approach. Progress in Brain Research, 174, pp. 137-150.

Kelley, A. E., & Berridge, K. C. (2002). The neuroscience of natural rewards: relevance to addictive drugs. The Journal of Neuroscience, 22 (9), pp. 3306-3311.

Kostopoulos, K., Chouvarda, I., Koutkias, V., Kokonozi, A., van Gils, M., & Maglaveras, N. (2011). An Ontology-based Framework Aiming to Support Personalized Exercise Prescription: Application in Cardiac Rehabilitation. Proceedings of the 33rd Annual International Conference of the IEEE EMBS, pp. 1567-1570.

Reinbolt, J., Haftka, R., Chmielewski, T., & Fregly, B. (2007). Are Patient-Specific Joint and Inertial Parameters Necessary for Accurate Inverse Dynamics Analyses of Gait? IEEE Transactions on Biomedical Engineering, 54 (5), pp. 782-793.

Schonauer, C., Pintaric, T., Kaufmann, H., Jansen-Kosterink, S., & Vollenbroek-Hutten, M. (2011). Chronic pain rehabilitation with a serious game using multimodal input. Proceedings of the 2011 International Conference on Virtual Rehabilitation (ICVR), pp. 1-8.

Schuurink, E., Houtkamp, J., & Toet, A. (2008). Engagement and EMG in Serious Gaming: Experimenting with Sound and Dynamics in the Levee Patroller Training Game. Proceedings of the 2nd International Conference on Fun and Games, pp. 139-149.

Solway, A., & Botvinick, M. M. (2012). Goal-directed decision making as probabilistic inference: A computational framework and potential neural correlates. Psychological Review, 119 (1), pp. 120-154.

Subirats, L., & Ceccaroni, L. (2011). An ontology for computer-based decision support in rehabilitation. MICAI'11 Proceedings of the 10th Mexican international conference on Advances in Artificial Intelligence, 1, pp. 549-559.

Thelen, D., & Anderson, F. (2006). Using computed muscle control to generate forward dynamic simulations of human walking from experimental data. Journal of Biomechanics, 39, pp. 1107-1115.

Thelen, D., Anderson, F., & Delp, S. (2003). Generating dynamic simulations of movement using computed muscle control. Journal of Biomechanics, 36, pp. 321-328.

Wang, Y., & Winters, J. (2005). A Dynamic Neuro-Fuzzy Model Providing Bio-State Estimation and Prognosis Prediction for Wearable Intelligent Assistants. Journal of NeuroEngineering and Rehabilitation, 2 (15), pp. 1-17.

Novak, D., Ziherl, J., Olenšek, A., Milavec, M., Podobnik, J., Mihelj, M., et al. (2010). Psychophysiological Responses to Robotic Rehabilitation Tasks in Stroke. IEEE Transactions on Neural Systems and Rehabilitation Engineering, 18 (4), pp. 351-361.

* cited by examiner

IN-HOME PATIENT-FOCUSED REHABILITATION SYSTEM

CROSS-REFERENCE TO RELATED APPLICATIONS

This is a Non-Provisional patent application of 62/163,286, filed on May 18, 2015, the entirety of which is hereby incorporated by reference.

BACKGROUND OF INVENTION

(1) Field of Invention

The present invention relates to a rehabilitation system and, more particularly, to a rehabilitation system that facilitates cost-effective in-home access to rehabilitation technologies that are currently available only at rehabilitation clinics under the supervision of trained physical therapists and technicians.

(2) Description of Related Art

Conventional clinic-based rehabilitation under the supervision of trained physical therapists and technicians can be both costly and inconvenient for individuals requiring care. There have been previous attempts to leverage inexpensive sensing components for rehabilitation (see the List of Cited Literature References, Literature Reference Nos. 6 and 18). However, the attempts tend to focus exclusively on biomechanical properties. While developmental work has been performed in assessing subject cognitive and emotional state, this has been limited to the domain of serious gaming (see Literature Reference Nos. 13 and 19), and not rehabilitation.

Furthermore, an expert system that can infer internal states (e.g., pain) in, real-time from external measurements has been prototyped (see Literature Reference No, 24). However, the system has not been integrated into an in-home rehabilitation system. With respect to knowledge representation, some work has been performed in the context of rehabilitation ontologies (see Literature Reference Nos. 16 and 21). Again, this has not been integrated into a larger system for in-home rehabilitation.

Finally, most in-home systems suggested in the literature have addressed stroke rehabilitation (see Literature Reference No. 10) and not musculoskeletal injuries, which affect a significant proportion of rehabilitation patients.

Thus, a continuing need exists for a rehabilitation system that takes into account emotional, cognitive, and biomechanical aspects of an individual which can be utilized by individuals with musculoskeletal injuries in a non-clinical setting. SUMMARY OF INVENTION The present invention relates to a rehabilitation system and, more particularly, to a rehabilitation system that facilitates cost-effective in-home access to rehabilitation technologies that are currently available only at rehabilitation clinics under the supervision of trained physical therapists and technicians. The system comprises one or more processors and a memory having instructions such that when the instructions are executed, the one or more processors perform multiple operations. The system monitors, using a Mobile Patient Monitor (MFM), a patient in real-time to generate a quantitative assessment of a physical state and a motivational state of the patient using sensor data obtained from a plurality of sensors. Using a Virtual Patient (VP) unit, predictions related to the patient are generated utilizing patient-specific biomechanical and neurocognitive models implemented with predictive simulations. Rehabilitation guidance is generated using a Virtual Coach (VC) unit through real-time communication with the VP unit. Using an Augmented Reality (AR) unit, video feed of the patient is registered with sensor data from the MPM and a set of simulation data from the VP unit. Rehabilitation guidance instructions are conveyed to the patient through dialog-based patient-VC interactions.

In another aspect, rehabilitation guidance is provided to the patient via a lightweight exoskeleton worn by the patient.

In another aspect, at least one biomechanical state prediction is generated with the VP unit using a set of motion and force measurements obtained with the MPM.

In another aspect, the system processes the sensor data and a set of patient profile data for use as simulation inputs to the VP unit. Model-based quantitative assessments of the patient's physical state and motivational state are generated using the simulation inputs. The model-based quantitative assessments are stored in a patient data archive, and simulations are performed to reveal biomechanical and neurocognitive information related to the patient.

In another aspect, the system abstracts a set of multi-dimensional time series vectors from the sensor data. A Virtual Patient Cognitive Model (VPCM) of the VP unit processes the set of multi-dimensional time series vectors. A set of cognitive state estimates are generated from the set of multi-dimensional time series vectors. The system determines how the set of cognitive state estimates affect rehabilitation treatment outcomes through processing of the set of cognitive state estimates by the VC unit in order to choose a strategy for desired patient results. A dynamic patient profile, comprising the determined effect of the set of cognitive state estimates, is stored in a rehabilitation knowledge base.

In another aspect, the VC unit guides the patient through rehabilitation treatment by applying a set of rehabilitation knowledge to a patient's specific needs through interaction with the VP unit. Candidate therapeutic actions are generated using the set of rehabilitation knowledge. The patient-specific biomechanical and neurocognitive models evaluate likely outcomes if the candidate therapeutic actions are taken.

In another aspect, the VP unit generates a plurality of simulation feeds related to the patient. A first simulation feed represents a patient reference avatar, mirroring the patient's motion. A second simulation feed represents a patient goal avatar, representing motion that the VC unit is guiding the patient toward.

Finally, the present invention also includes a computer program product and a computer implemented method. The computer program, product includes computer-readable instructions stored on a non-transitory computer-readable medium that are executable by a computer having one or more processors, such that upon execution of the instructions, the one or more processors perform the operations listed herein. Alternatively, the computer implemented method includes an act of causing a computer to execute such instructions and perform the resulting operations.

BRIEF DESCRIPTION OF THE DRAWINGS

The objects, features and advantages of the present invention will be apparent from the following detailed descriptions of the various aspects of the invention in conjunction with reference to the following drawings, where.

DETAILED DESCRIPTION

Figure 1:
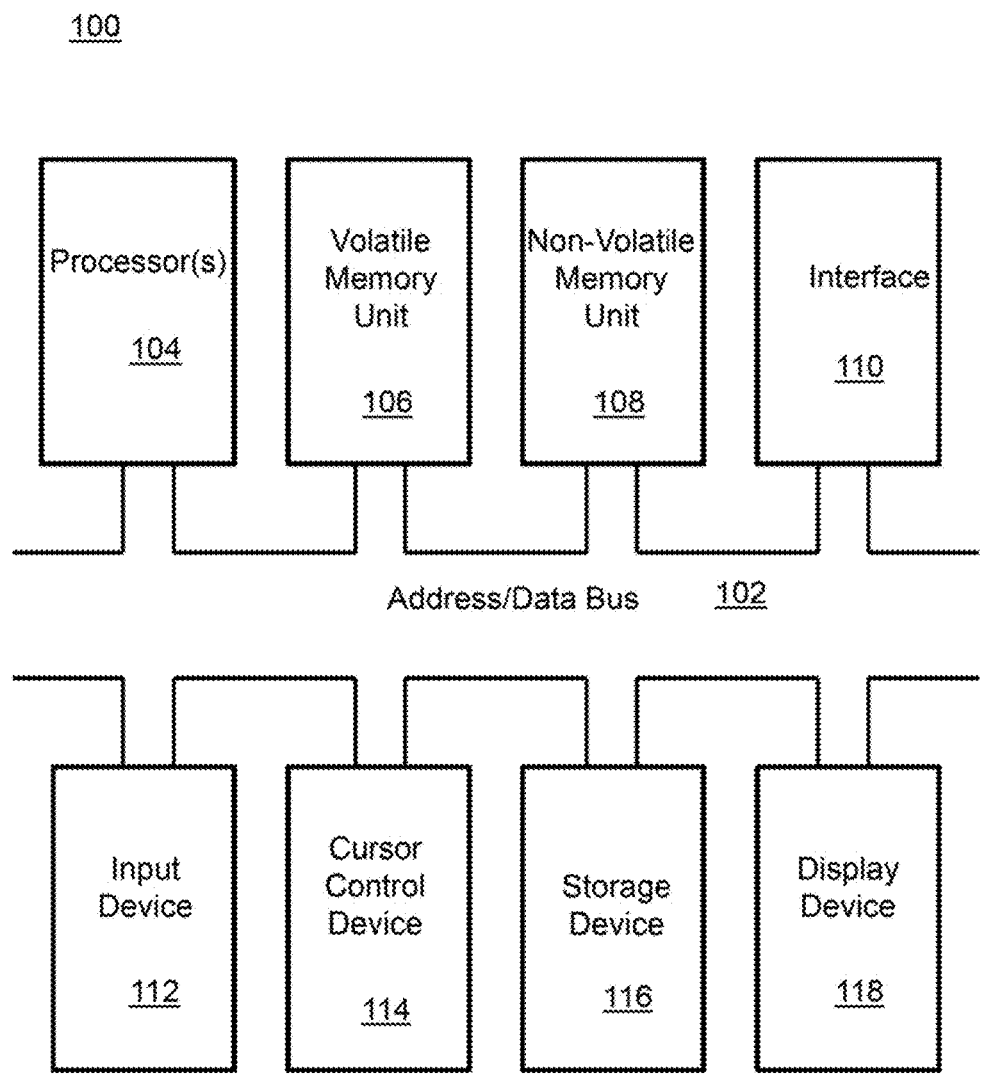
FIG. 1 is a block diagram depicting the components of a rehabilitation system according to embodiments of the present disclosure.

The present invention relates to a rehabilitation system and, more particularly, to a rehabilitation system that facilitates cost-effective in-home access to rehabilitation technologies that are currently available only at rehabilitation clinics tinder the supervision of trained physical therapists and technicians.

The following description is presented to enable one of ordinary skill in the art to make and use the invention and to incorporate it in the context of particular applications. Various modifications, as well as a variety of uses in different applications will be readily apparent to those skilled in the art, and the general principles defined herein may be applied to a wide range of aspects. Thus, the present invention is not intended to be limited to the aspects presented, but is to be ti accorded the widest scope consistent with the principles and novel features disclosed herein.

In the following detailed description, numerous specific details are set forth in order to provide a more thorough understanding of the present invention. However, it will be apparent to one skilled in the art that the present invention may be practiced without necessarily being limited to these specific details. In other instances, well-known structures and devices are shown in block diagram form, rather than in detail, in order to avoid obscuring the present invention.

The reader's, attention is directed to all papers and documents which are filed concurrently with this specification and which are open to public inspection with this specification, and the contents of all such papers and documents are incorporated herein by reference. All the features disclosed in this specification, (including any accompanying claims, abstract, and drawings) may be replaced by alternative features serving the same, equivalent or similar purpose, unless expressly stated otherwise. Thus, unless expressly stated otherwise, each feature disclosed is one example only of a generic series, of equivalent or similar features. Furthermore, any element in a claim that does not explicitly state "means for" performing a specified function, or "step for" performing a specific function, is not to be interpreted as a "means" or "step" clause as specified in 35 U.S.C. Section 112, Paragraph 6. In particular, the use of "module," step of or "act of" in the claims herein is not intended to invoke the provisions of 35 U.S.C. Paragraph 6.

Before describing the invention in detail, first a list of cited references is provided. Next, a description of the various principal aspects of the present invention is provided. Finally, specific details of various embodiment of the present invention are provided to give an understanding of the specific aspects.

(1) List of Cited Literature References

The following references are cited throughout this application. For clarity and convenience, the references are listed herein as a central resource for the reader. The following references are hereby incorporated by reference as though fully set forth herein. The references are cited in the application by referring to the corresponding literature reference number.

1. Anselme, P. (2010). The uncertainty processing theory of motivation. *Behavioural Brain Research*, 208 (2), 291-310.
2. Axelrod, L., Fitzpatrick, G., Balaam, M., Mawson, S., Burridge, J., Ricketts, I., et al. (2011). A toolkit to explore lived experience of motivation: When words are not enough. *Proceedings of the 5th International Conference on Pervasive Computing Technologies for Healthcare*, (pp. 32-39).
3. Balaam, M., Rennick Egglestone, S., Fitzpatrick, G., Rodden, T., Hughes, A., Wilkinson, A., et al. (2011). Motivating mobility: designing for lived motivation in stroke rehabilitation. *Proceedings of the 2011 Conference on Human Factors in Computing Systems*, (pp. 3073-3082).
4. Berridge, K. C. (2004). Motivation concepts in behavioral neuroscience. *Physiology & Behavior*, 81 (2), 179-209.
5. Brown, J. W., Reynolds, J. R., & Braver, T. S. (2007). A computational model of fractionated conflict-control mechanisms in task-switching. *Cognitive Psychology*, 55 (1), 37-85.
6. Chang, C., Lange, B., Zhang, M., Koenig, S., Requejo, P., Somboon, N., et al. (2012). Towards pervasive physical rehabilitation using Microsoft Kinect. 2012 *6th International Conference on Pervasive Computing Technologies for Healthcare (PervasiveHealth)*, (pp. 159-162).
7. Clark, R. B., Pua, Y., McCrory, P., Bennell, K., & Hunt, M. (2010). Validity and reliability of the Nintendo Wii Balance Board for assessment of standing balance. *Gait & Posture*, 31 (3), 307-310.
8. Delp, S., Anderson, F., Arnold, A., Loan, P., Habib, A., John, C., et al. (2007). OpenSim: Open-Source Software to Create and Analyze Dynamic Simulations of Movement. *IEEE Transactions on Biomedical Engineering*, 54 (11), 1940-1950.
9. Edginton, K., Güler, H. O., & Berme, N. (2008). *Instrumented Treadmills: Reducing the Need for Gait Labs*. White Paper, Bertec Corporation.
10. Egglestone, S. R., Axelrod, L., Nind, T., Turk, R., Wilkinson, A., Burridge, J., et al. (2009). A design framework for a home-based stroke rehabilitation system: identifying the key components. *Proceedings of the 3rd International Conference on Pervasive Computing Technologies for Healthcare*, (pp. 1-8).
11. Frank, M. J. (2011). Computational models of motivated action selection in corticostriatal circuits. *Current Opinion in Neurobiology*, 21 (3), 381-386.

12. Fregly, B., Reinbolt, J., Rooney, K., Mitchell, K., & Chmielewski, T. (2007). Design of patient-specific gait modifications for knee osteoarthritis rehabilitation. *IEEE Transactions on Biomedical Engineering*, 54 (9), 1687-1695.
13. Jercic, P., Astor, P., Adam, M., & Hilborn, O. (2012). A serious game using physiological interfaces for emotion regulation training in the context of financial decision-making. *Proceedings of the European Conference of Information Systems*.
14. Johnson, J. G. (2009). Embodied cognition of movement decisions: a computational modeling approach. *Progress in Brain Research*, 174, 137-150.
15. Kelley, A. E., & Berridge, K. C. (2002). The neuroscience of natural rewards: relevance to addictive drugs. *The Journal of Neuroscience*, 22 (9), 3306-3311.
16. Kostopoulos, K., Chouvarda, I., Koutkias, V., Kokonozi, A., van Gils, M., & Maglaveras, N. (2011). An Ontology-based Framework Aiming to Support Personalized Exercise Prescription: Application in Cardiac Rehabilitation. *Proceedings of the 33rd Annual International Conference of the IEEE EMBS*, (pp. 1567-1570).
17. Reinbolt, J., Haftka, R., Chmielewski, T., & Fregly, B. (2007). Are Patient-Specific Joint and Inertial Parameters Necessary for Accurate Inverse Dynamics Analyses of Gait? *IEEE Transactions on Biomedical Engineering*, 54 (5), 782-793.
18. Schonauer, C., Pintaric, T., Kaufmann, H., Jansen-Kosterink, S., & Vollenbroek-Hutten, M. (2011). Chronic pain rehabilitation with a serious game using multimodal input. *Proceedings of the 2011 International Conference on Virtual Rehabilitation (ICVR)*, (pp. 1-8).
19. Schuurink, E., Houtkamp, J., & Toet, A. (2008). Engagement and EMG in Serious Gaming: Experimenting with Sound and Dynamics in the Levee Patroller Training Game. *Proceedings of the 2nd International Conference on Fun and Games*, (pp. 139-149).
20. Solway, A., & Botvinick, M. M. (2012). Goal-directed decision making as probabilistic inference: A computational framework and potential neural correlates. *Psychological Review*, 119 (1), 120-154.
21. Subirats, L., & Ceccaroni, L. (2011). An ontology for computer-based decision support in rehabilitation. *MICAI'11 Proceedings of the 10th Mexican international conference on Advances in Artificial Intelligence, I*, pp. 549-559.
22. Thelen, D., & Anderson, F. (2006). Using computed muscle control to generate forward dynamic simulations of human walking from experimental data. *Journal of Biomechanics*, 39, 1107-1115.
23. Thelen, D., Anderson, F., & Delp, S. (2003). Generating dynamic simulations of movement using computed muscle control. *Journal of Biomechanics*, 36, 321-328.
24. Wang, Y., & Winters, J. (2005). A Dynamic Neuro-Fuzzy Model Providing Bio-State Estimation and Prognosis Prediction for Wearable Intelligent Assistants. *Journal of NeuroEngineering and Rehabilitation*, 2 (15), 17.
25. Novak, D., Ziherl, J., Olenšek, A., Milavec, M., Podobnik, J., Mihelj, M., et al. (2010). Psychophysiological Responses to Robotic Rehabilitation Tasks in Stroke. *IEEE Transactions on Neural Systems and Rehabilitation Engineering*, 18 (4), 351-361

(2) Principal Aspects

Various embodiments of the invention include three "principal" aspects. The first is a rehabilitation system. The system is typically in the form of a computer system operating software or in the form of a "hard-coded" instruction set. This system may be incorporated into a wide variety of devices that provide different functionalities. The second principal aspect is a method, typically in the form of software, operated using a data processing system (computer). The third principal aspect is a computer program product. The computer program product generally represents computer-readable instructions stored on a non-transitory computer-readable medium such as an optical storage device, e.g., a compact disc (CD) or digital versatile disc (DVD), or a magnetic storage device such as a floppy disk or magnetic tape. Other, non-limiting examples of computer-readable media include hard disks, read-only memory (ROM), and flash-type memories. These aspects will be described in more detail below.

A block diagram depicting an example of a system (i.e., computer system 100) of the present invention is provided in FIG. 1. The computer system 100 is configured to perform calculations, processes, operations, and/or functions associated with a program or algorithm. In one aspect, certain processes and steps discussed herein are realized as a series of instructions (e.g., software program) that reside within computer readable memory units and are executed by one or more processors of the computer system 100. When executed, the instructions cause the computer system 100 to perform specific actions and exhibit specific behavior, such as described herein.

The computer system 100 may include an address/data bus 102 that is configured to communicate information. Additionally, one or more data processing units, such as a processor 104 (or processors), are coupled with the address/data bus 102. The processor 104 is configured to process information and instructions. In an aspect, the processor 104 is a microprocessor. Alternatively, the processor 104 may be a different type of processor such as a parallel processor, application-specific integrated circuit (ASIC), programmable logic array (PLA), complex programmable logic device (CPLD), or a field programmable gate array (FPGA).

The computer system 100 is configured to utilize one or more data storage units. The computer system 100 may include a volatile memory unit 106 (e.g., random access memory ("RAM"), static RAM, dynamic RAM, etc.) coupled with the address/data bus 102, wherein a volatile memory unit 106 is configured to store information and instructions for the processor 104. The computer system 100 further may include a non-volatile memory unit 108 (e.g., read-only memory ("ROM"), programmable ROM ("PROM"), erasable programmable ROM ("EPROM"), electrically erasable programmable ROM "EEPROM"), flash memory, etc.) coupled with the address/data bus 102, wherein the non-volatile memory unit 108 is configured to store static information and instructions for the processor 104. Alternatively, the computer system 100 may execute instructions retrieved from an online data storage unit such as in "Cloud" computing. In an aspect, the computer system 100 also may include one or more interfaces, such as an interface 110, coupled with the address/data bus 102. The one or more interfaces are configured to enable the computer system 100 to interface with other electronic devices and computer systems. The communication interfaces implemented by the one or more interfaces may include wireline (e.g., serial cables, modems, network adaptors, etc.) and/or wireless (e.g., wireless modems, wireless network adaptors, etc.) communication technology.

In one aspect, the computer system 100 may include an input device 112 coupled with the address/data bus 102, wherein the input device 112 is configured to communicate information and command selections to the processor 100.

In accordance with one aspect, the input device 112 is an alphanumeric input device, such as a keyboard, that may include alphanumeric and/or function keys. Alternatively, the input device 112 may be an input device other than an alphanumeric input device. In an aspect, the computer system 100 may include a cursor control device 114 coupled with the address/data bus 102, wherein the cursor control device 114 is configured to communicate user input information and/or command selections to the processor 100. In an aspect, the cursor control device 114 is implemented using a device such as a mouse, a track-ball, a track-pad, an optical tracking device, or a touch screen. The foregoing notwithstanding, in an aspect, the cursor control device 114 is directed and/or activated via input from the input device 112, such as in response to the use of special keys and key sequence commands associated with the input device 112. In an alternative aspect, the cursor control device 114 is configured to be directed or guided by voice commands.

In an aspect, the computer system 100 further may include one or more optional computer usable data storage devices, such as a storage device 116, coupled with the address/data bus 102. The storage device 116 is configured to store information and/or computer executable instructions. In one aspect, the storage device 116 is a storage device such as a magnetic or optical disk drive (e.g., hard disk drive ("HDD"), floppy diskette, compact disk read only memory ("CD-ROM"), digital versatile disk ("DVD")). Pursuant to one aspect, a display device 118 is coupled with the address/data bus 102, wherein the display device 118 is configured to display video and/or graphics. In an aspect, the display device 118 may include a cathode ray tube ("CRT"), liquid crystal display ("LCD"), field emission display ("FED"), plasma display, or any other display device suitable for displaying video and/or graphic images and alphanumeric characters recognizable to a user.

The computer system 100 presented herein is an example computing environment in accordance with an aspect. However, the non-limiting example of the computer system 100 is not strictly limited to being a computer system. For example, an aspect provides that the computer system 100 represents a type of data processing analysis that may be used in accordance with various aspects described herein. Moreover, other computing systems may also be implemented. Indeed, the spirit and scope of the present technology is not limited to any single data processing environment. Thus, in an aspect, one or more operations of various aspects of the present technology are controlled or implemented using computer-executable instructions, such as program modules, being executed by a computer by one or more processors. In one implementation, such program modules include routines, programs, objects, components and/or data structures that are configured to perform particular tasks or implement particular abstract data types. In addition, an aspect provides that one or more aspects of the present technology are implemented by utilizing one or more distributed computing environments, such as where tasks are performed by remote processing devices that are linked through a communications network, or such as where various program modules are located in both local and remote computer-storage media including memory-storage devices.

Figure 2:
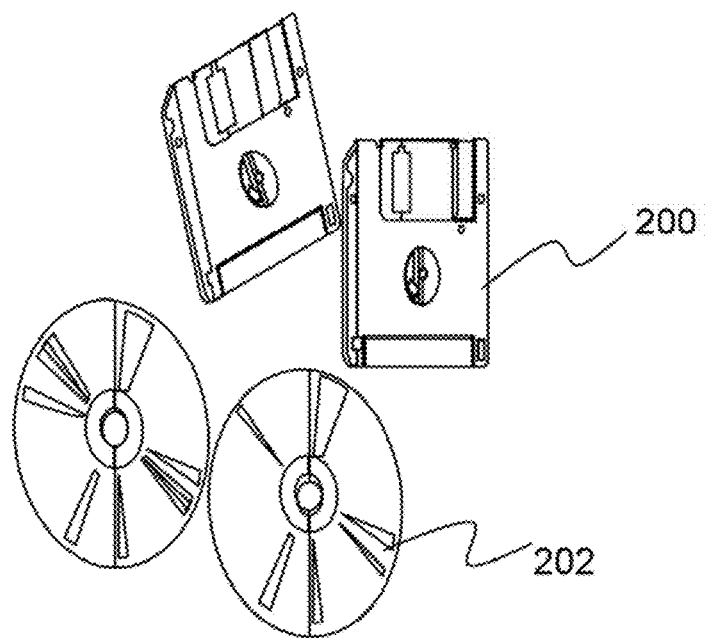
FIG. 2 is an illustration of a computer program product according to embodiments of the present disclosure.

An illustrative diagram of a computer program product (i.e., storage device) embodying the present invention is depicted in FIG. 2. The computer program product is depicted as floppy disk 200 or an optical disk 202 such as a CD or DVD. However, as mentioned previously, the computer program product generally represents computer-readable instructions stored on any compatible non-transitory computer-readable medium. The term "instructions" as used with respect to this invention generally indicates a set of operations to be performed on a computer, and may represent pieces of a whole program or individual, separable, software modules. Non-limiting examples of "instruction" include computer program code (source or object code) and "hard-coded" electronics (i.e. computer operations coded into a computer chip). The "instruction" is stored on any non-transitory computer-readable medium, such as in the memory of a computer or on a floppy disk, a CD-ROM, and a flash drive. In either event, the instructions are encoded on a non-transitory computer-readable medium.

(3) Specific Details of Various Embodiments

Described is a unique integration of four key components that, in combination, represent a system for in-home access to rehabilitation technologies. The first component is a Mobile Patient Monitor (MPM) incorporating portable multi-modal physiological sensing technologies capable of self-administered setup and use in homes. This component monitors both physical state and cognitive/emotional state elicited from different sensing modalities, thus providing a sensor-based assessment of the patient's physical and motivational state. The MPM streams patient physiological data in real-time to the second component, a Virtual Patient (VP) unit comprised of patient-specific biomechanical and neurocognitive models implemented within simulation to predict patient motivational and physical state, rehabilitation performance, and future rehabilitation outcomes. The patient-specific nature of the VP unit's biomechanical and cognitive models provides the capability of responsiveness to the evolution of the individual patient's recovery. The VP unit also facilitates clinician access of digital patient rehabilitation data from each in-home session.

The third component of the system according to embodiments of the present disclosure, a Virtual Coach (VC) unit, has access to clinician defined patient-specific therapy goals as well as physiological data and predictive biomechanical and neurocognitive simulations through real-time communication with the VP unit. The VC unit uses the VP unit as a resource to guide rehabilitation by assessing actual patient motivation, physical performance, and rehabilitation progress against predictive simulations and running "what if" scenarios for different rehabilitation protocols. This is done during the rehabilitation session and offline as an extensive post-therapy analysis of the entire session to allow planning for future sessions. The VC unit maintains a dynamic patient profile and patient specific rehabilitation rule base, including inferences made about the particular patient and his/her progress. This knowledge is stored in a rehabilitation knowledge base that can be queried at any time by the VC unit as well as by clinicians monitoring the in-home progress. The guidance generated by the VC unit is conveyed to the patient using dialog-based interactions involving a VC unit avatar providing textual, gestural, and audible instructions. The patient will also be able to use this mechanism to communicate with, and respond to queries (elicitation of patient feedback) from, the VC unit.

The fourth component according to embodiments of the present disclosure is an Augmented Reality (AR) unit that combines a video feed of the patient overlaid with sensor and simulation data. Visual guidance from the VC unit, including desired patient movements, is accurately registered with video imagery in the form of a virtual mirror. Real-time guidance is also conveyed to the patient in the form of kinesthetic cues from tactile or electrical stimulation sources using a lightweight training exoskeleton.

Individual components of the system described herein can be undocked for flexible use outside of the in-home rehabilitation system. For example, the VP unit could be equipped with a graphical user interface for direct use by a physical therapist (PT) in a rehabilitation clinic, allowing the therapist to have access to predictive biomechanical and neurocognitive simulation and quantitative analysis of the patient. The VC unit, with its dynamic patient profile and rehabilitation rule base, could also be used in a clinical setting as a digital PT assistant, providing the clinical therapist with access to extensive expert knowledge about the patient. The VC unit could also be used to aid in the training of rehabilitation professionals.

Figure 3:
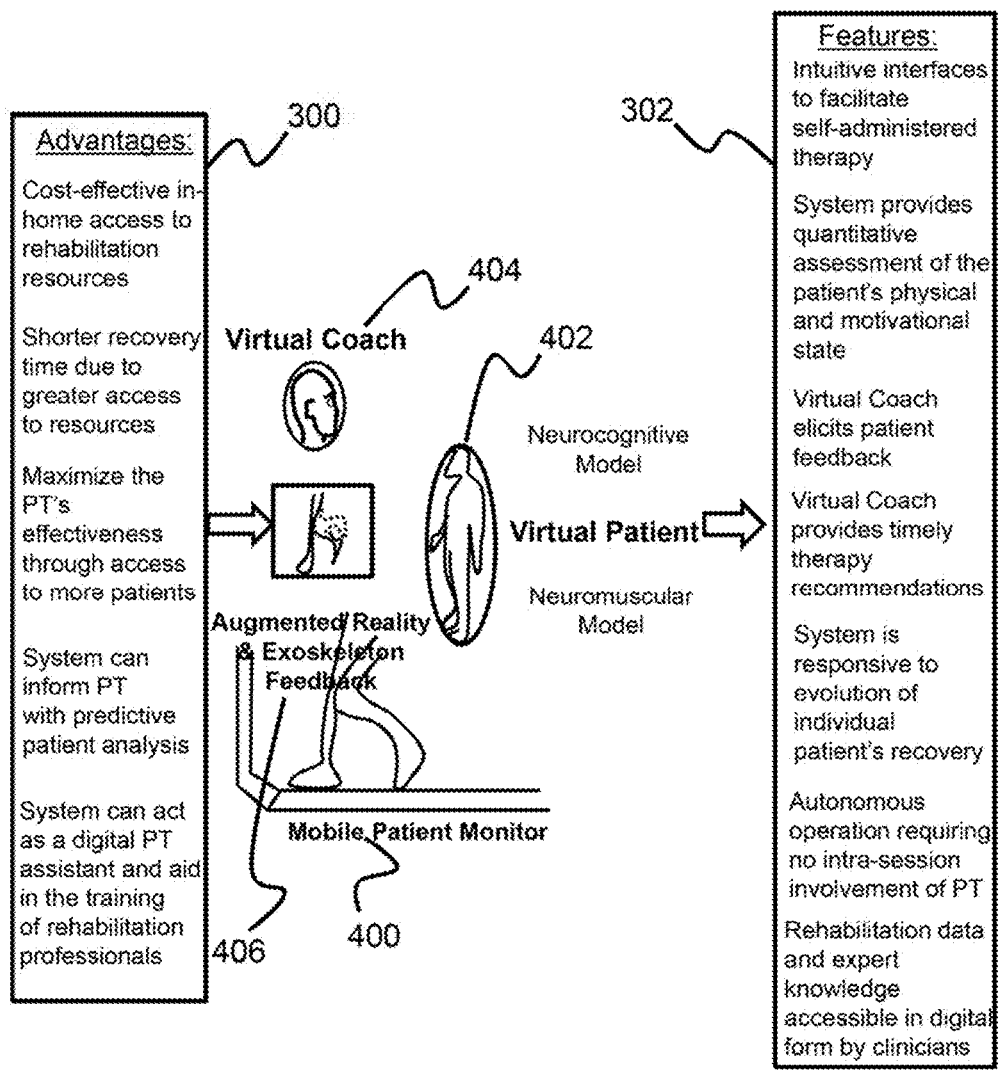
FIG. 3 is an illustration of advantages of the in-home rehabilitation system according to embodiments of the present disclosure.

One purpose of the present invention is to facilitate cost-effective in-home access to rehabilitation technologies that are currently available only at rehabilitation clinics under the supervision of trained physical therapists and technicians. This will provide advantages over conventional clinic-based rehabilitation, including shorter recovery time due to greater access to rehabilitation resources and technologies, as well as maximizing the physical therapist's effectiveness by enabling access to more patients. FIG. 3 provides a list of advantages 300 and a list of features 302 of the in-home rehabilitation system according to embodiments of the present disclosure and illustrates integration of a MPM 400, a VP unit 402, a VC unit 404, and an AR unit 406, each of which are described in detail below.

Significant benefits exist over traditional clinic-based rehabilitation. While such a system may still necessitate clinical visits, the number of these visits could be substantially reduced. Since rehabilitation clinics are typically located in metropolitan areas, travel time to and from the clinic would be reduced. If the patient needs to be driven by a family member or friend, this reduces the burden on those people as well.

Figure 4:
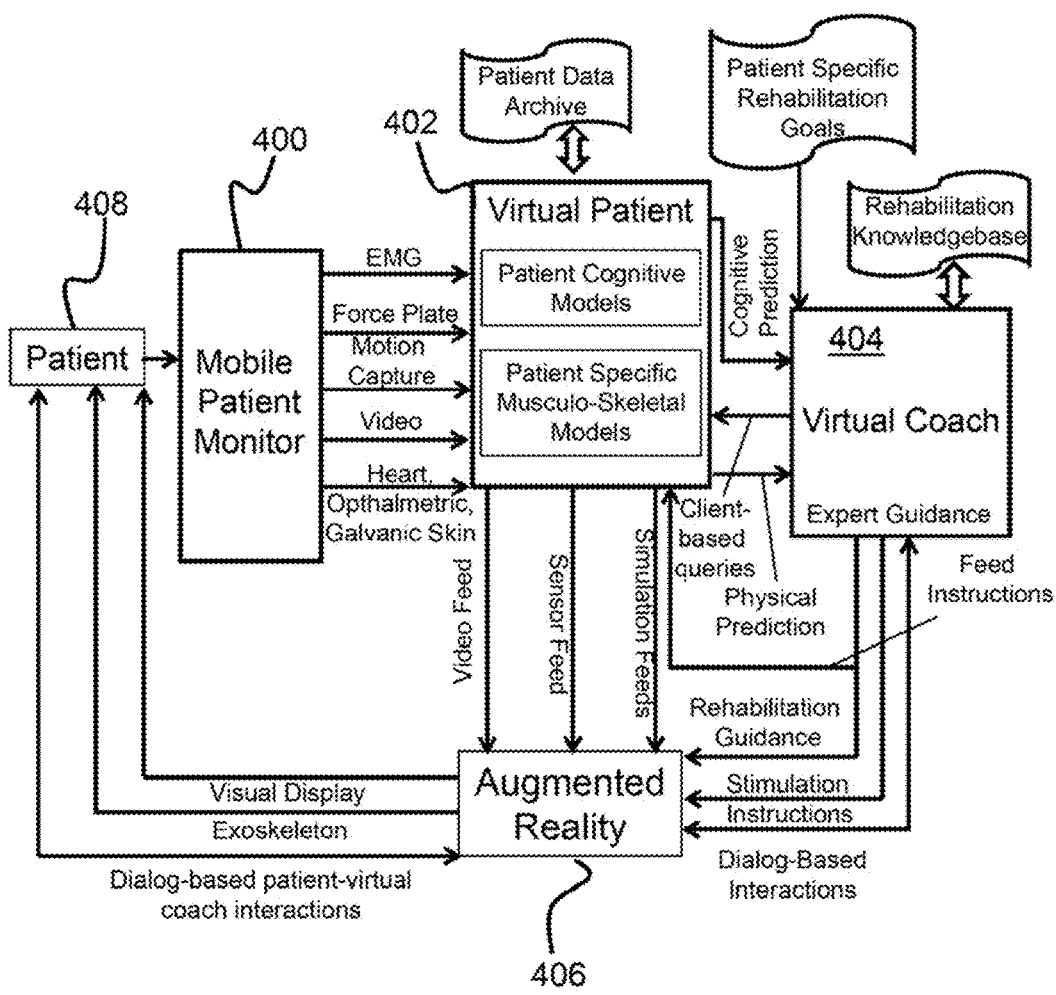
FIG. 4 is a flow diagram illustrating the architecture for an in-home rehabilitation system according to embodiments of the present disclosure.

The overall system architecture of the system according to embodiments of the present disclosure is depicted in FIG. 4. It comprises mobile multi-modal physiological sensing (MPM 400) integrated with patient-specific biomechanical and neurocognitive simulations (VP unit 402) and performance-based guidance (VC unit 404) to provide effective in-home rehabilitation using dialog-based patient-VC interactions. An Augmented Reality unit 406 provides visual and kinesthetic cues, through a lightweight training exoskeleton, to the patient 408. Each of the units/sub-systems is described in further detail below. For the purposes of the invention, a unit or sub-system is defined as one or more data processors of a computer system operating a series of instructions (e.g., software program) that reside within computer readable memory units and are executed by the one or more processors of the computer system.

(4.1) The Mobile Patient Monitor

Figure 5:
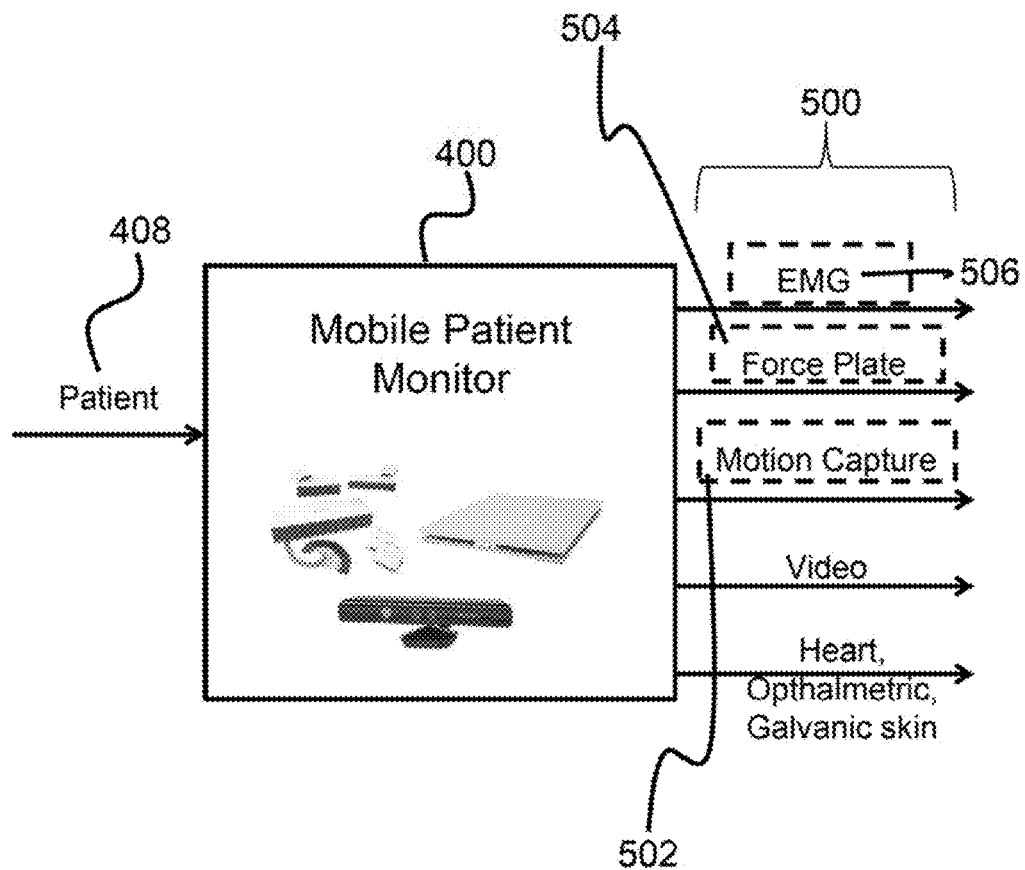
FIG. 5 is an illustration of a Mobile Patient Monitor according to embodiments of the present disclosure.

The Mobile Patient Monitor (MPM) 400 is the conduit between the actual patient 408 and the VP unit 402. It provides the VP unit 402 with physiological data streams that are used in conjunction with patient specific simulations to generate a data rich digital representation of the patient 408. More specifically, the MPM 400 comprises an integrated suite of portable sensors and a data acquisition system. These sensors are self-administered. They provide a quantitative assessment of physical and motivational state through direct measurement of physiological signals. FIG. 5 illustrates examples of key sensing modalities 500 of the MPM 400, including, but not limited to force plate information, electromyography (EMG), motion capture, video, and heart, opthalmetric, and galvanic skin information. A desktop/laptop computer can be used to run the MPM software.

The MPM 400 is a portable physiological sensor suite capable of easy setup and use in homes, enabling a rich understanding of patient state by the VP unit 402 and more relevant feedback by the VC unit 404 to the patient 408. Motion capture, force plate, and EMG data are used downstream in the system to characterize the biomechanical state of the patient. Other sensing, including heart rate, eye tracking, and galvanic skin response are used for characterizing emotional effects, such as motivation and fatigue.

The MPM 400 comprises existing sensing modalities 500 to assess the biomechanical state and cognitive state of the patient 408. One or more of motion capture, force plate, and EMG modalities are incorporated for helping to characterize the biomechanical state of the rehabilitation patient, while one or more of heart rate, respiration, opthalmetrics, and galvanic skin response (GSR) are incorporated for helping to characterize the cognitive state of the patient.

A motion capture system 502 may form an integral component of the MPM 400, as it provides patient configurational data to the VP unit 402. While optical marker based motion capture systems are among the most accurate, they are not practical for self-administration in an in-home system and typically cost between $100,000 and $200,000. For the MPM 400, relatively inexpensive markerless systems are specified that leverage three-dimensional (3D) cameras, such as the Microsoft Kinect produced by Microsoft located at One Microsoft Way, Redmond, Wash., 98052-6399.

Force plates 504 may be another integral component of the MPM 400. Along with patient motion data, external force data may be critical in making biomechanical state predictions in the VP unit 402, particularly with regard to gait rehabilitation. Low-end systems like the Wii Balance Board (produced by Nintendo located at 4600 150th Ave NE Redmond, Wash. 98052) are quite effective and reliable compared to professional systems (see Literature Reference No. 7). Force plates have also been integrated into high-end instrumented treadmills. While having the same form factor as consumer grade treadmills designed for home environments, force instrumented treadmills are currently cost prohibitive (on the order of $100,000) for an in-home system. However, they are becoming more accessible and economical, and they are reducing the need for clinical gait labs (see Literature Reference No. 9). A lower cost alternative to instrumented treadmills is force-sensing walkways. The AMTI AccuGait Portable Force Platform and Walkway (produced by AMTI, Inc. located at 176 Waltham Street, Watertown, Mass. 02472) is a non-limiting example of a system with a data acquisition system that meets the requirements for the MPM 400, although lower-end systems may also be suitable.

In addition to motion and force measurements, EMG 506 may be incorporated into the MPM 400. EMG 506 is useful in biomechanical state prediction for determining temporal patterns in the activation of muscle groups. It can also be used to help validate computational predictions of muscle activations and forces. Muscle fatigue can also be inferred from increases in EMG 506 activity. In one aspect, a portable desktop system (e.g., Bagnoli desktop EMG system produced by DELSYS, Inc. located at 23 Strathmore Road, Natick, Mass., 01760) is incorporated into the MPM 400.

With regard to cognitive state, a variety of physiological sensors can assist in eliciting this information. For example, increased heart rate and respiration are signs of fatigue or pain. Increased galvanic skin response and opthalmetrics, such as pupil diameter, have also been linked to stress or surprise. Professional grade systems are portable, moderately priced, and specified for incorporation into the MPM 400. It is noted that not all sensing modalities will need to be used at all times in the in-home rehabilitation system. Motion capture 502 is integral to the rehabilitation process and will be continuously used; however, some of the other sensors will be employed as the specific rehabilitation protocol dictates.

(4.2) The Virtual Patient

Figure 6:
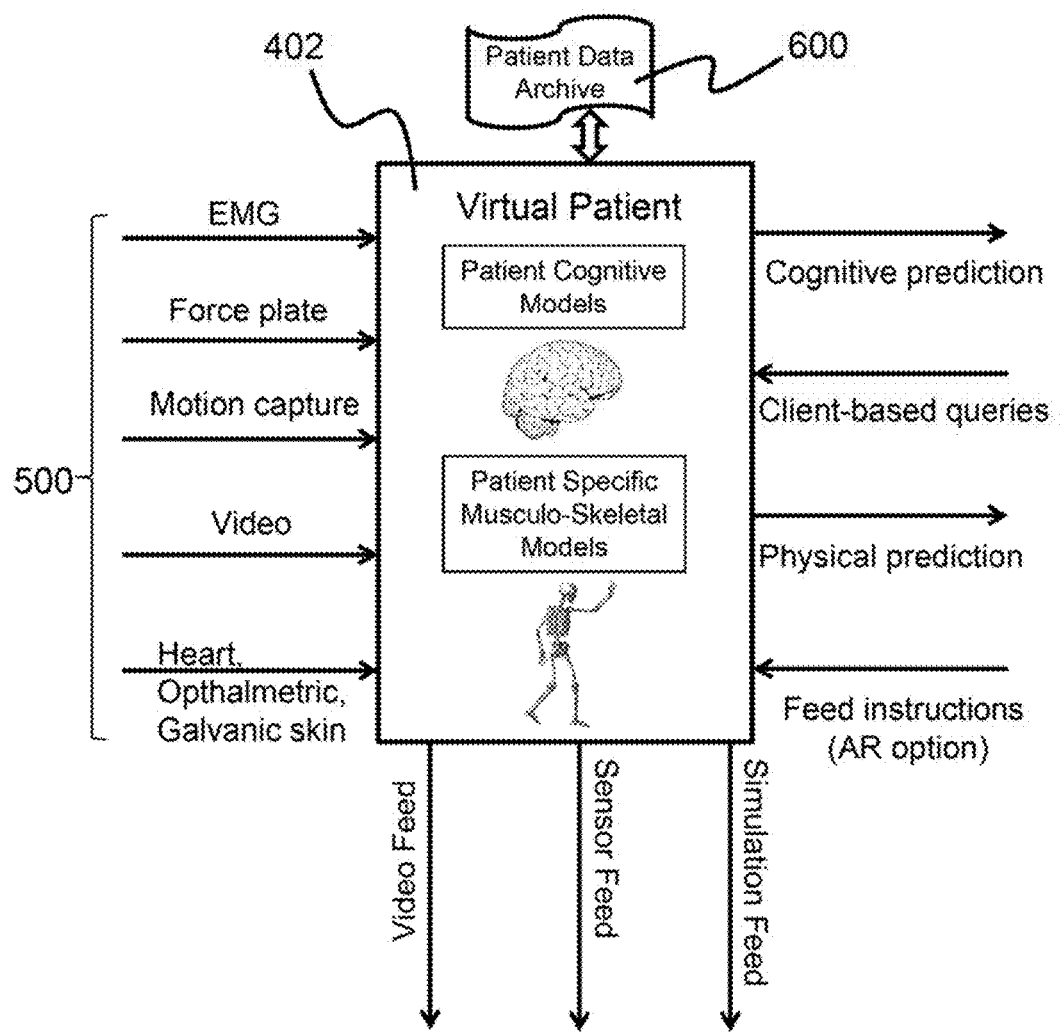
FIG. 6 is an illustration of a Virtual. Patient unit comprising patient musculoskeletal and neurocognitive models according to embodiments of the present disclosure.

The Virtual Patient (VP) unit 402, shown in FIG. 6, comprises a dynamic digital representation of the rehabilitation patient. Inputs to the VP unit 402 include physiological sensor data from sensing modalities 500 as well as patient profile data. These data streams are processed and used as simulation inputs to patient specific biomechanical and cognitive models, thus providing model-based quantitative assessments of the patient's physical and motivational state. A patient data archive 600 of all relevant patient data input to and generated by the VP unit 402 provides a technique for rehabilitation data preservation and facilitates clinician access. Based on physiological data input from the MPM 400, the VP unit 402 performs simulations to reveal extensive biomechanical and neurocognitive information about the patient. Forward looking "what if" simulations can also be performed to assess therapy alternatives.

The VP unit 402 comprises patient-specific musculoskeletal models and a simulation environment with full state computation of skeletal dynamics and Hill-type active state musculotendon models. Patient-specific neurocognitive models and a neurocognitive simulation architecture are additional components of the VP unit 402. Each of these aspects are described in detail below. A desktop/laptop computer can be used to run the VP unit 402 software.

(4.2.1) Virtual Patient Biomechanical Model

Figure 7:
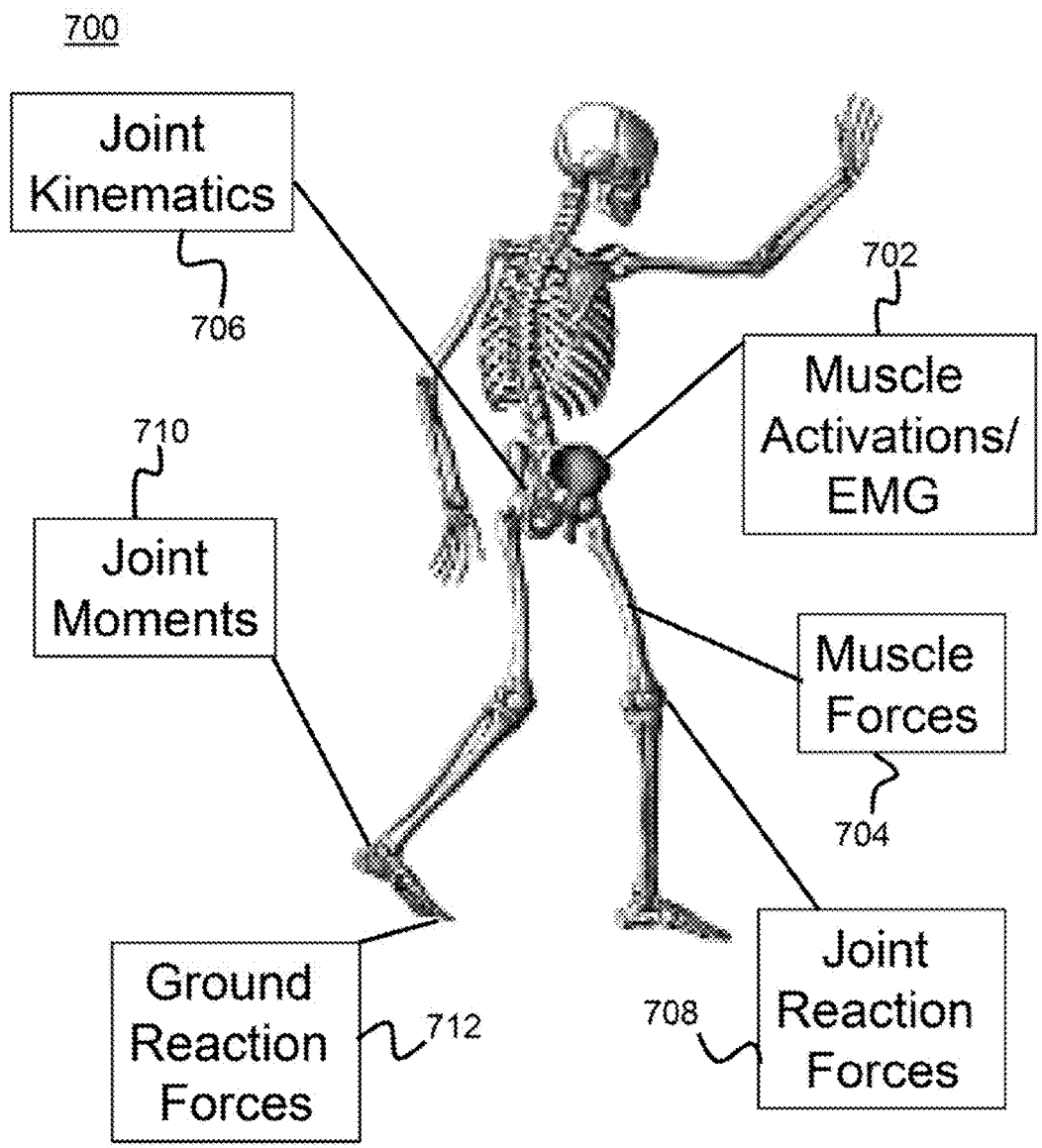
FIG. 7 is an illustration of a Virtual Patient Biomechanical Model according to embodiments of the present disclosure.

The biomechanical sub-component of the VP unit 402, the Virtual Patient Biomechanical Model (VPBM) 700 depicted in FIG. 7, functions to simulate the rehabilitation patient's musculoskeletal state. This provides the capability of quantitative assessment of the patient's physical state that complements the physiological data from the VP unit 402 by computing internal variables that are unobservable or difficult to observe using sensors. Specifically, the VPBM 700 quantitatively characterizes muscle activations 702, muscle forces 704, strains, and moment arms, as well as joint torques/kinematics 706 and joint reaction forces 708/joint moments 710 (both internal to the joints and ground reaction forces 712). Additionally, with the incorporation of fatigue models and metabolic models, the VPBM 700 is able to characterize loss of muscle strength and response due to fatigue as well as muscle metabolic expenditure. Additionally, forecasting future states in the VPBM 700 will provide a technique for the VC unit 404 to choose the best therapeutic actions given a set of candidates that can be tested in simulation (e.g., biomechanical output produced by Open-Sim).

OpenSim (described in Literature Reference No. 8), an existing open-source musculoskeletal simulation environment built on C++ libraries using a formal application programming interface (API), is an example biomechanical simulation engine of the VPBM 700 (although other musculoskeletal simulation engines could also be used). A procedure for generating patient-specific biomechanical models is also incorporated into the VPBM 700. This is based on published work related to determining patient-specific parameters (see Literature Reference Nos. 12 and 17). It is expected that the procedure for generating the patient-specific model will be performed at the rehabilitation clinic prior to the patient receiving the in-home system. It could also potentially be performed as part of an initial in-home setup. The computed muscle control algorithms (described in Literature Reference Nos. 22 and 23 as well as U.S. patent application Ser. No. 14/539,898, which is hereby incorporated by reference as though fully set forth herein) are used within the musculoskeletal simulation environment to generate neuromuscular controls to drive the patient-specific models in forward simulations.

As a non-limiting example of how the VPBM 700 will operate during a therapy session, consider a patient undergoing gait rehabilitation. In order for the VC unit 404 to make informed therapeutic decisions, it needs a characterization of the patient's current physical state. The VPBM 700 will provide this by making the full musculoskeletal system state available at a given time point, given partial input data from the MPM 400 (i.e., motion capture and force plate data). This will reveal variables relevant to the patient's therapy goals and specific musculoskeletal injuries, including information related to physical overload. Such information would include estimated reaction forces at key joints that have been injured, and muscle-tendon forces at key areas of musculotendon injury. The VC unit 404 would be able to use this information to actively modify the pace of rehabilitation. Additionally, the VPBM 700 simulations would provide forecasts that would help the VC unit 404 decide on longer-term therapeutic actions based on expected outcomes.

(4.2.2) Virtual Patient Cognitive Model

Figure 8:
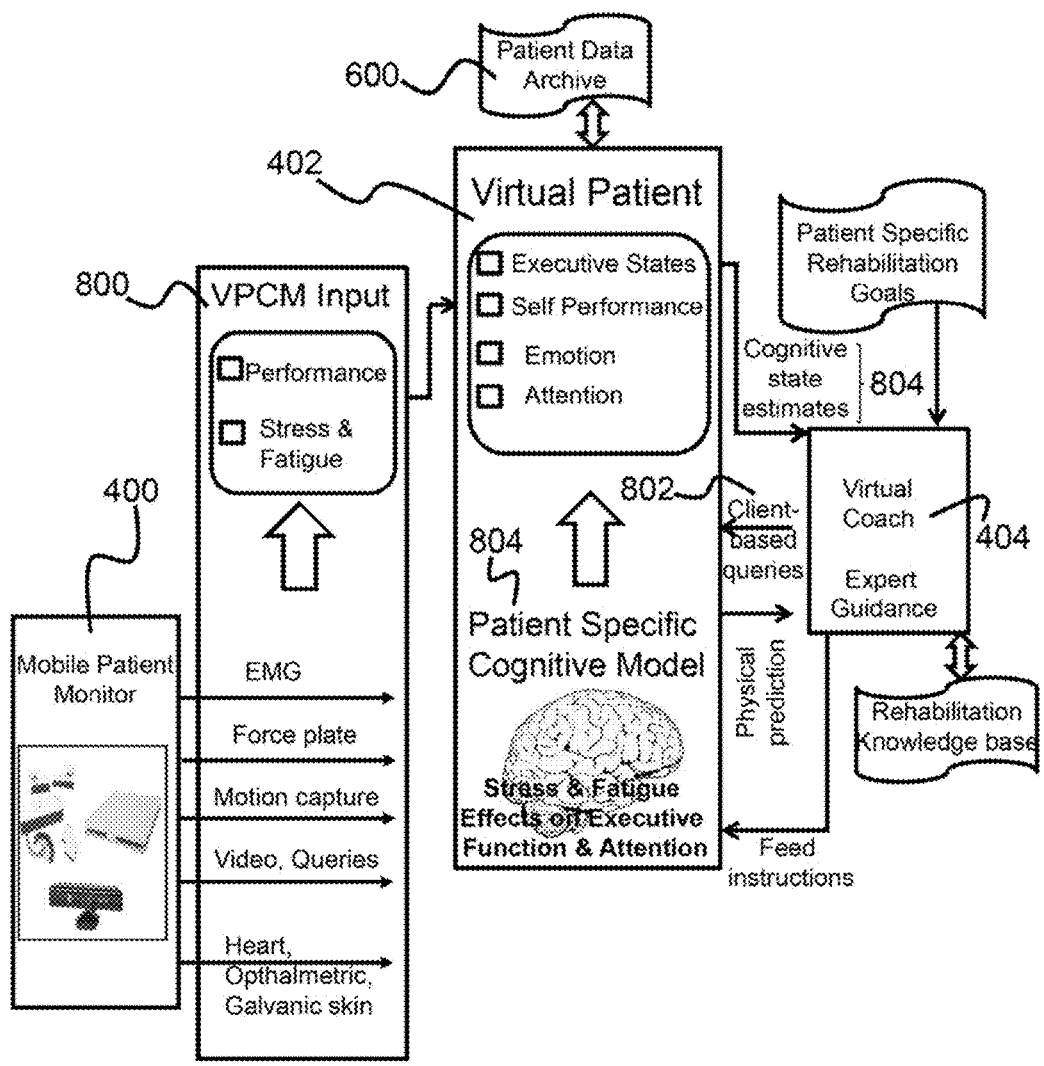
FIG. 8 is an illustration of interactions between a Mobile Patient Monitor, a Virtual Patient Cognitive Model, a Virtual Patient unit, and a Virtual Coach unit according to embodiments of the present disclosure.

As depicted in FIG. 8, the Virtual Patient Cognitive Model (VPCM) 800 is the neurocognitive sub-component of the VP unit 402 that simulates and predicts the patient's cognitive state so the VC unit 404 can inform and adapt rehabilitation therapies in real-time. The VPCM 800 is used to simulate the short and long-term cognitive states of the patient allowing the VC unit 404 to test potential therapies. The VPCM 800 is a brain-based cognitive-model designed to predict the cognitive state of the patient from the physiological signals acquired by the MPM 400, and verified by client-based queries 802 and the physical therapist.

The interaction between the MPM 400, the VPCM 800, and the VC unit 404 is shown in FIG. 8. The inputs to the VPCM 800 are two high-level signals from the MPM 400 decoded from patient measurements, and the outputs of the VPCM 800 are cognitive state estimates 804. The VPCM 800 operates in two modes, current and future, for cognitive state estimation. The current mode operates continuously using the most recent VPCM 800 inputs to offer cognitive state estimates 804 for the patient in the form of a vector with confidence values, keeping the VPCM 800 in synchronization with the patient. Future mode provides forecasts of cognitive state estimates 804, by adding a temporal dimension to the current model vector. The VPCM's 800 optimization for patient specific cognitive models occurs in both modes by learning mechanisms, described below, which are driven to increase confidence values both in current and future modes.

As shown in FIG. 8, the MPM 400 acquires a variety of signals from the patient. The input to the VPCM 800 includes two high-level multi-dimensional time series vectors (performance and stress/fatigue vectors) derived from the patient signals. These time series vectors are generated in response to the measured patient signals. A non-limiting example of these time series would be time series of joint angles and muscle activations from EMG. These time series could be further augmented by highlighting high or low values in each time series or abrupt changes, for instance. During a training period, conventional machine learning is used to associate measured patient signals with level of performance, and stress and fatigue. For example, specific levels of EMG activity and galvanic skin response may indicate heightened levels of stress for a patient. This association would be learned during initial patient training. These are performance and stress and fatigue vectors. The VP unit 402 contains the VPCM 800 and VPBM (not shown). The VPCM also produces multi-dimensional time series vectors for use by the VC unit 404 as a window into the patient's 1) executive states, 2) self-performance, 3) emotions, and 4) attentional states. These high-level vectors are produced from the patient specific cognitive model 804, which learns to reflect the individual patient over time. As the forecasting power of patient-specific models 804 are validated over rehabilitation sessions, they enter the patient data archive 600. This creates both better initial models for new patients, and informs clinicians why cognitive states in rehabilitation therapies lead to successful treatments.

The forecasting capability of the VPCM 800 in future mode is useful to explore the space of rehabilitation therapies and their effects on patient cognitive states. In essence, the VPCM 800 acts as a powerful forward model, predicting how patient cognitive states would evolve with the two important factors in rehabilitation: a candidate therapy and changes in patient state through simulated VPCM 800 input data (e.g., high stress and fatigue). Forecasting allows the VC unit 404 to choose the best strategy over a wide range of possibilities for the best short and long term results. This will bootstrap future mode learning in the VPCM 800 using data observed in the rehabilitation sessions. Finally, because of this continuous optimization of the VPCM 800 as therapy progresses, the explanatory power of patient-specific cognitive models 804 becomes greater. The VPCM 800 can be used not only to predict which therapies have the best outcome, but also why they are effective for specific individuals. Over the long term, as the patient data archive 600 grows, the VPCM 800 will allow clinicians to better understand why certain cognitive states evolve and lead to the success of therapy strategies. In turn, the knowledge gained can return to adapt a superior VC unit 404.

During initial rehabilitation training, the VPCM 800 patient-specific cognitive state predictions (element 500) will be compared to the patient's cognitive state as assessed by a trained Physical Therapist. The VPCM 800 will learn (standard machine learning) from differences between the estimated cognitive states and the therapist assessed cognitive states until it can accurately predict the response within 75% before in-home rehabilitation begins (see FIG. 8). The responses to questionnaires (queries) are important inputs to the VPCM 800. They serve as target cognitive states that the model can learn to accurately estimate over time. During in-home rehabilitation, patients will occasionally be queried for their mental state by the VC unit 404 so the therapy can be adapted as the model learns individual causal relationships between biometric signals and cognitive states. However, due to high levels of inconsistencies in self-reporting of patients with musculoskeletal injuries, during any future clinic-based sessions the trained physical therapist will reassess the patient's cognitive state to ensure a VPCM 800 cognitive state prediction accuracy greater than or equal to 75% (see Literature Reference No. 25).

Tracking patient state using the MPM 400 assures patient safety, optimizes therapy, and provides comparison data for post-session quantitative analysis. The VPCM 800 augments these capabilities by linking measured patient states from the MPM 400 with hidden cognitive states using the VPCM 800. Both the performance and stress and fatigue model states track several variables that range from purely physiological to cognitive states that are linked to VPCM 800 state predictions. For example, expended energy by the patient from the observed kinematic variables from motion capture provides input about metabolic costs in self-performance in the VPCM 800. The perception of costs and rewards effects motivation states, shapes goal states, and ultimately determines how a patient decides to perform during therapy.

Figure 9:
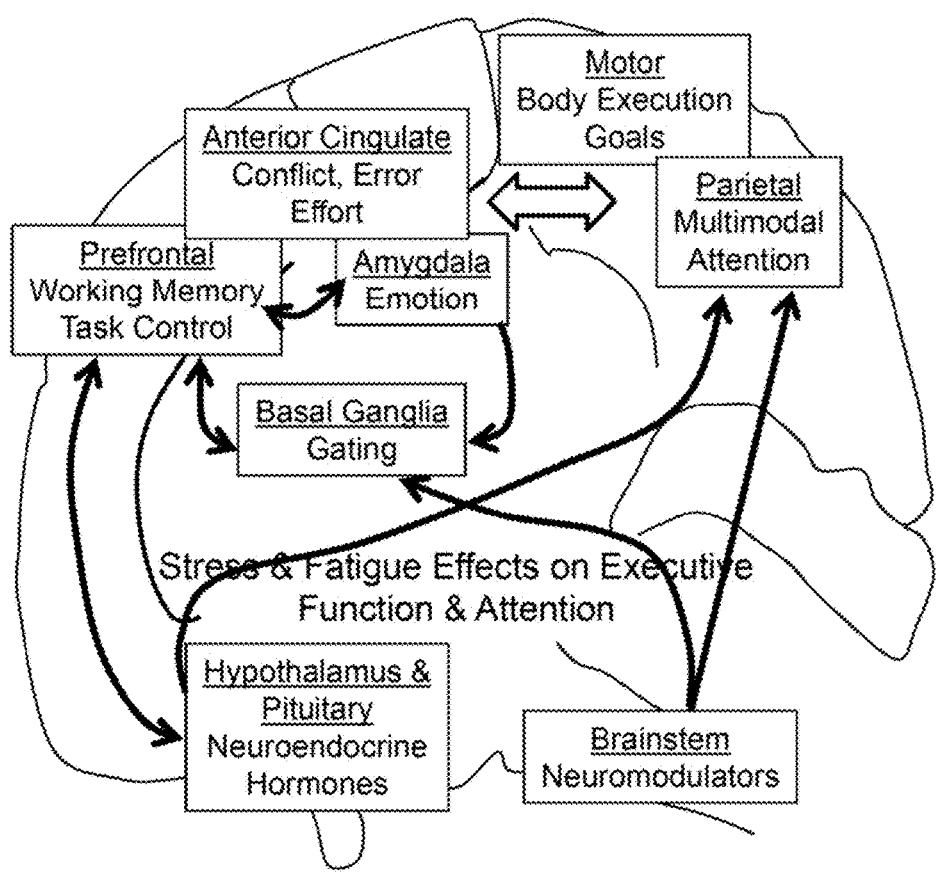
FIG. 9 is an illustration of a patient specific cognitive model according to embodiments of the present disclosure.

As shown in FIG. 9, of the Patient Specific Cognitive Model 804 of the VPCM 800 incorporates three major brain regions: executive (prefrontal, anterior cingulate, amygdala, basal ganglia), attention (motor, parietal), and neuroendocrine and neuromodulatory (hypothalamus and pituitary, brainstem) to accurately track and predict the patient's attentional, emotional (motivational), performance, and executive states. Stress and fatigue information from the neuroendocrine and neuromodulatory centers modulate the executive and attentive regions and their processes. Actions are selected within the executive region where internal connections compute emotional, error, and conflict values. The attentive region focuses multimodal attention towards task information (e.g., feedback) as well as execution of motor actions and goals. Each brain area endows the VPCM 800 with a specific functionality and tracks patient-specific internal variables. This regional division endows the VPCM 800 with the necessary cognitive and physiological functionality to predict the patient's cognitive state with a high degree of explanatory power. These functions are critical elements to model the motivational, executive, and self-performance states under realistic attentional and emotional control (see Literature Reference No. 14). Furthermore, similar brain region based models have been shown to be critical in learning and predicting the emotional and cognitive influences on executive states and performance goals (see Literature Reference Nos. 11 and 20). The description of the neural areas, their computations, and interactions for each major area are shown in FIG. 9.

The prefrontal cortex (PFC) is critical for maintaining the patient's high-level goals and goal states within working memory. It influences the patient's actions though goal-directed inputs from the basal ganglia (see Literature Reference No. 20). The memories are subject to a dynamic load capacity limit in the PFC. The basal ganglia (BG) is a critical brain region necessary to functionally gate actions from the PFC into the motor cortex. The amygdala is necessary to regulate the emotional context with inputs to both the BG and PFC (see Literature Reference No. 11). The anterior cingulate cortex (ACC) monitors the reward (i.e., VC feedback) the patient receives, the effort the patient expends (metabolic cost), the error in performance, and conflict arising from alternate choices during task execution (see Literature Reference No. 5). These internal variables are required by the VPCM 800 to make accurate real-time assessments of the patient's self-performance and emotional state.

To predict motivational state, the parietal cortex (PC) is necessary to track the patient's attentional state with multimodal parameters utilizing eye tracking (visual attention) reaction time and error rate changes. In order to track the patient's physical state and interface with the VPBM 800, the motor cortex is needed to processes body execution commands and motor goals. The VPCM 800 will be able to predict a decrease in the fidelity of the motor cortex commands when stress, pain, and a lack of either attention or motivation are detected.

The brainstem-neuromodulatory systems are central in the dynamic regulation of attention in the PC and ACC. This occurs through acetylcholine released by cholinergic neurons in the basal forebrain, producing online conflict and error measures of performance and motivational selection of seeking behavior (see Literature Reference No. 1). The hypothalamus and pituitary systems are critical for regulating stress and the patient's emotional state, directly affecting motivational levels, through direct inputs to the PFC and PC (see Literature Reference Nos. 4 and 15).

As a non-limiting example of how the VPCM 800 will operate during a therapy session, consider a case where a patient has been performing at or above the session goals, but late in the session becomes physically exhausted and begins to lose motivation to continue the session. The goals and working memories within the PFC are unchanged; however, when the patient loses motivation neither are maintained at optimal levels (working memory load decreases) and they are not as effectively gated by the BG into the motor cortex. When the patient continues to perform in a demotivated state, stress and pain levels rise in the hypothalamus and pituitary system, as predicted by the VPCM 800 and post validated by stress and fatigue state vector's GSR (galvanic skin response) derived measures. Attentional focus begins to decline within the PC as measured by eye-tracking. Decreased motivation and attention, and increased stress and pain decrease the effectiveness of reward and increase conflict as error rates rise in the ACC.

The ability for the patient specific cognitive model 804 to progress over time is vital. The patient specific cognitive model 804 will provide the Virtual Coach unit 404 with the capability to mimic a therapist's capacity to adapt exercise tasks to fit the patient's mental and physical abilities during rehabilitation. The changes in patient motivation may depend on the time of day the patient is using the system, from day-to-day depending on external personal factors, and over longer periods of time as physical abilities change (see Literature Reference Nos. 2 and 3). Differences will also occur between individuals as their tolerance of pain, fatigue, and attention fluctuates in response to changes in motor functional capabilities. The VPCM 800 inputs will guide the patient specific cognitive model 804 to use these fluctuations in the data to model better training techniques encouraging the patient's rehabilitation. By comparing the response of the VPCM 800 inputs with the expected future forecast by the patient specific cognitive model 804, the system will learn if the patient is responding as predicted or if the models should be adapted because of the unexpected patient responses. The patient inquiries will also be an important part of this feedback, allowing the VPCM 800 to decide to continue using the current model and adapt the future forecast to affect the short and long-term rehabilitation.

(4.3) The Virtual Coach

Figure 10:
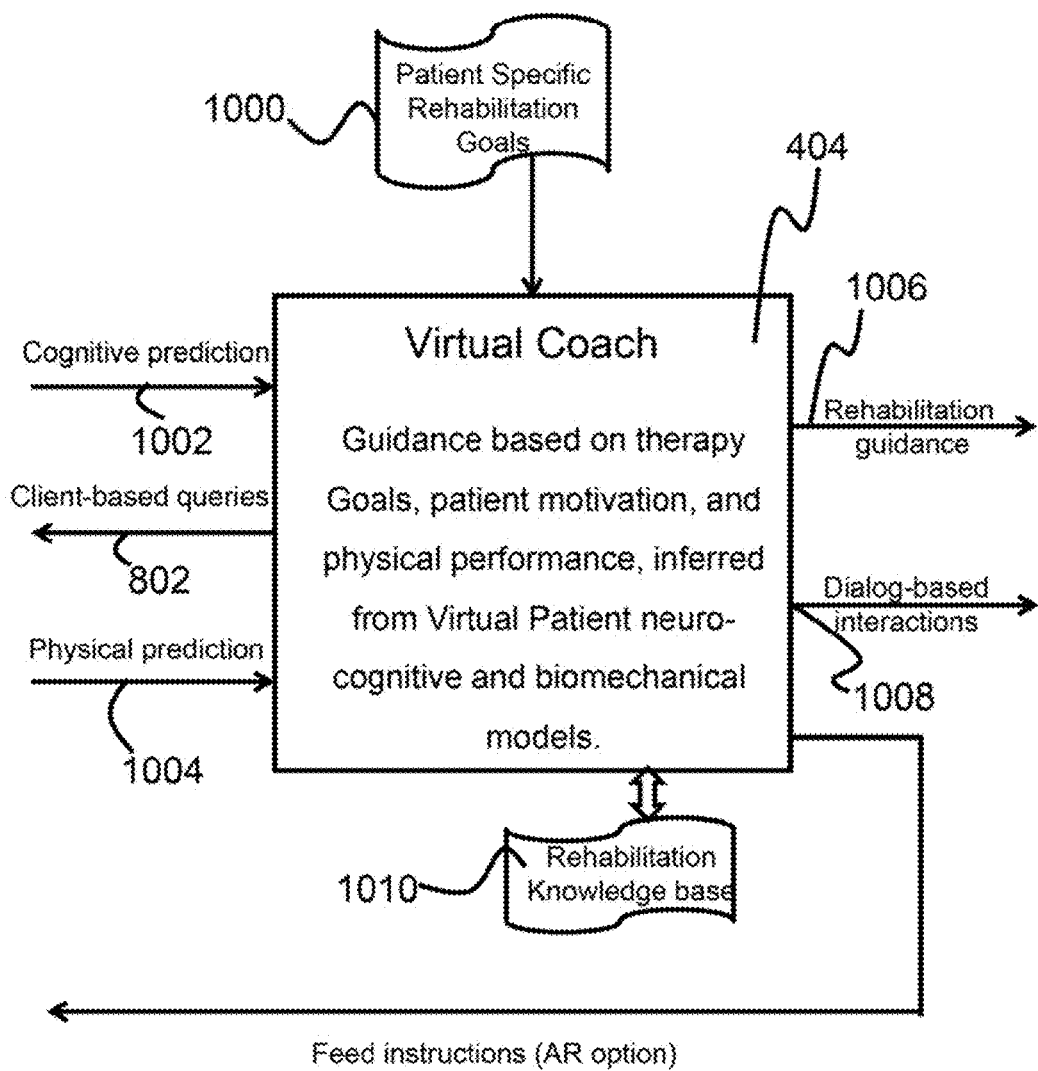
FIG. 10 is an illustration of a Virtual Coach unit according to embodiments of the present disclosure.
Figure 11:
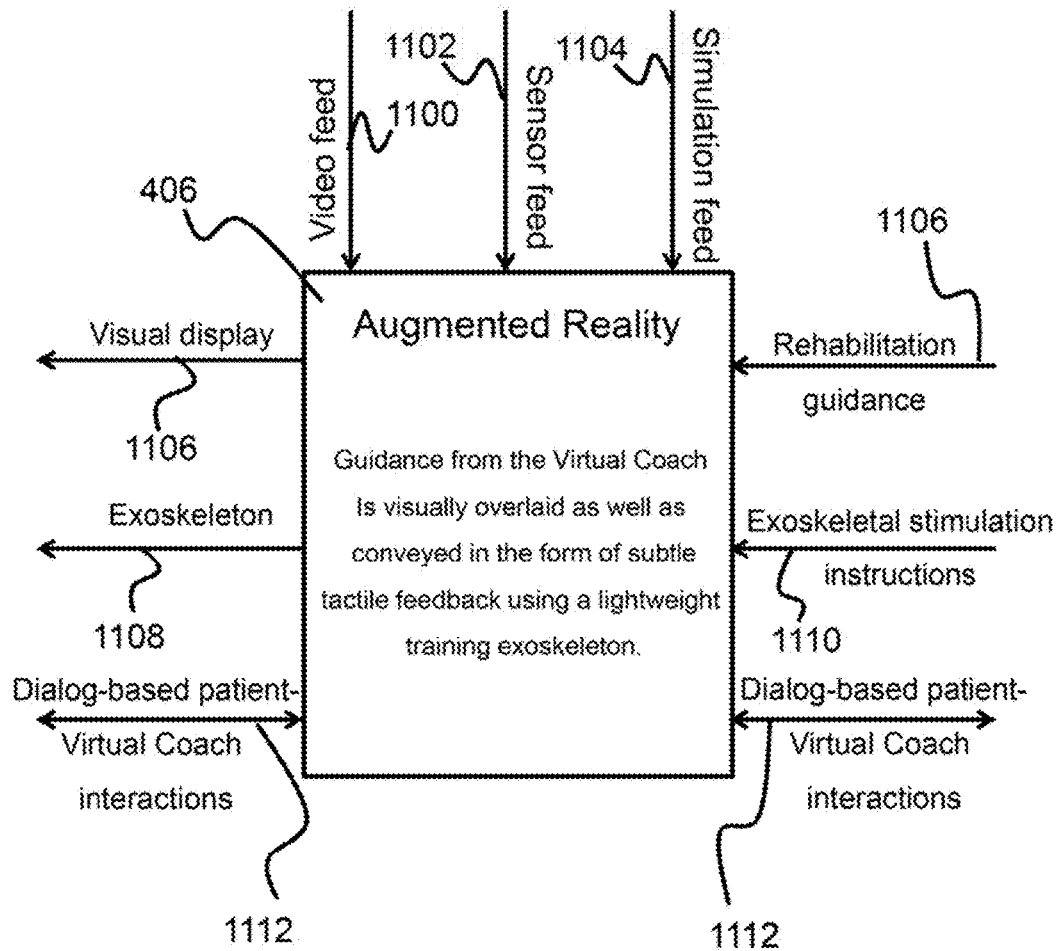
FIG. 11 is an illustration of an Augmented Reality unit according to embodiments of the present disclosure.

The Virtual Coach (VC) unit 404 receives input from the VP unit's 402 biomechanical and cognitive models to guide rehabilitation based on patient-specific therapy goals and patient performance. The VC unit 404 heavily leverages the resources of the VP unit 402. The cognitive state characterization of the VPCM 800 and the biomechanical state characterization of the VPBM 800, described in depth above, provide the core inputs to the VC unit 404. Interaction with the VC unit 404 has already been detailed in the discussion of the VPCM 800 above. Coupled with patient-specific rehabilitation goals 1000, and cognitive and physical information provided by the VP unit 402 (cognitive prediction 1002, client-based queries 802, physical prediction 1004), the VC unit 404 progressively modifies rehabilitation guidance 1006 it provides to the patient using dialog-based interactions 1008, as shown in FIG. 10. The VC unit 404 provides an expert system and rule base for providing patient guidance. A rehabilitation ontology and knowledge base 1010 stores expert learned knowledge. A knowledge base is a technology used to store complex structured and unstructured information used by a computer system. A desktop/laptop computer can be used to run the VC unit 404 software.

A client-server model facilitates communications between the VC unit 404 and the VP unit 402. The VC unit 404 acts as a client and submits client-based queries 802 to the VP unit 402. These queries 802 may comprise requests for current state predictions of the patient. The VC unit 404 heavily leverages the VP unit's 402 resources in current state prediction (cognitive prediction 1002 and physical prediction 1004) as well as extrapolating rehabilitation progress at various future stages in the therapy for different patient recovery conditions. In this way, the VC unit 404 uses the VP unit 402 as a resource for assessing actual rehabilitation progress against predictive simulations and running "what if" scenarios for different rehabilitation protocols. This can be done online during the rehabilitation session, or offline after the session as an extensive post-therapy analysis of the entire session and planning for future sessions.

(4.3.1) Core Reasoning Engine

The VC unit 404 is designed to guide a patient through the therapeutic process when their therapist is not present. To do so, the VC unit 404 uses generic rehabilitation knowledge and applies it to a specific patient's needs by interacting with the VP unit 402 for that patient. Together, the VC unit 404 and the VP unit 402 support a generate-and-test paradigm whereby expert rules are used to generate candidate therapeutic actions, and personalized patient biomechanical and cognitive models are used to evaluate the likely outcomes if these actions are taken. Once an action is selected, the VC unit 404 is able to monitor progress during therapy so that any deviation from the expected response can trigger adjustments to the patient's routine.

Given a set of patient rehabilitation goals 1000 provided by the patient's therapist, the VC unit 404 generates a set of near-term therapeutic actions that the patient might perform to help reach these goals. These actions are treated as a set of candidates that must first be tested before they are presented to the patient. For each candidate, a simulation is run within the VP unit 402 to estimate the combined physical and mental changes that may result from the recommended activity. The VP unit 402 then evaluates and scores each alternative both in terms of physical improvements as well as emotional response. For instance, some alternatives may yield rapid physical improvement but, because they are more stressful, the VPCM 800 might indicate that the patient is likely to become overly frustrated or discouraged. Alternatively, a less aggressive workout might yield too little progress to keep the patient interested. The VP unit 402 scoring is able to indicate which activities are ideally suited to provide an optimal combination of physical improvement and psychological commitment. Using these scores, the VC unit 404 ranks the alternatives that it generated, and selects the highest-ranking action to recommend to the patient.

When a therapy is selected, the VC unit 404 is able to use the real-time monitoring features of the VP unit 402 to track the progress of the patients against the expected trajectory determined from prior simulation of patient progress. As any deviations are detected, the VC unit 404 provides real-time adjustments to either slow down or accelerate the planned exercise routine. Also, the VPCM 800 is available to assist selection of encouragement messages or possible suppression messages to prevent injury to an overly enthusiastic patient.

The VC unit 404 stores a dynamic patient profile, including inferences made about the patient, in a rehabilitation knowledge base 1010 that can be queried at any time by the VC unit 404. Knowledge representation is an important component of the VC unit 404. It facilitates rule-based reasoning and knowledge dissemination to clinicians.

(4.4) The Augmented Reality Unit

The augmented reality (AR) unit 406, depicted in FIG. 1, renders accurately registered (pixel-level) patient video feed 1100, sensor feed 1102, simulation feed 1104, and visual guidance from the VC unit 404 on a large flat panel display (i.e., visual display 1106) at 30 Hertz (Hz) refresh rates with low latency to produce a mirror-like appearance to the patient. The AR unit 406 combines video feed 1100 of the patient overlaid with sensor (sensor feed 1102) and simulation data (simulation feed 1104). Rehabilitation guidance 1106 from the VC unit 404 is visually overlaid as well as conveyed to the patient in the form of subtle kinesthetic feedback/cues provided by a lightweight training exoskeleton 1108 from a tactile or electrical stimulation source. This exoskeleton 1108 can also provide direct information about biomechanical state, such as joint angles, for the VP unit 402. A desktop/laptop computer can be used to run the AR unit 406 software.

Assistive exoskeletons have recently become commercially available (such as from Ekso Bionics located at 1414 Harbour Way S #1201, Richmond, Calif., 94804). These systems are large and powerful given their requirement for providing substantial assistive forces to the user. The price of these systems is on the order of $150,000. Consequently, these systems are not considered practical for in-home rehabilitation. Additionally, the capabilities they provide are not in line with the in-home rehabilitation system according to the embodiments of the present disclosure. The present invention specifies a low-cost lightweight system that is largely passive but provides kinesthetic cues from a tactile or electrical stimulation source (e.g., exoskeletal stimulation instructions 1110). The exoskeleton 1108 will be worn as part of the AR unit 406. The intent is to augment the visual guidance to the patient with kinesthetic guidance, not provide active force assistance.

Based on feed instructions sent from the VC unit 404 to the VP unit (VPBM 700), the AR unit 406 synchronizes the patient video (video feed 1100) and VPBM 700 feeds generated by the VP unit 402. Sensor data (sensor feed 1102) is also annotated on the video/simulation overlay as well. The VC unit 404 uses this visual display 1106 to provide rehabilitation guidance 1106 to the patient. One simulation feed 1104 of the patient serves as the patient reference avatar mirroring the patient's motion but providing additional data. The additional data can include muscle activation patterns mapped as colors on the simulated muscles and joint loads mapped as force vector arrows at the joints. Another simulation feed 1104 serves as the patient goal avatar. The patient goal avatar represents the desired motion that the VC unit 404 is guiding the patient toward. This is based on an intermediate goal motion that the VC unit 404 chooses based on the patient's motivational and physical state, derived by the VPCM 800 and VPBM 700, respectively, as well as past performance progress and long-term rehabilitation goals. Localized kinesthetic stimulation in the exoskeleton augments and reinforces the visual guidance. A non-limiting example of localized kinesthetic stimulation includes vibration at a particular joint. stimulation (e.g., tactile actuators that vibrate on the skin to convey kinesthetic information to the patient at different locations on the body). The rehabilitation guidance 1106 generated by the VC unit 404 is conveyed to the patient using dialog-based interactions 1112 involving a VC unit 404 avatar providing textual, gestural, and audible instructions.

Components of the invention described herein have multiple applications. For example, the system according to embodiments of this disclosure can significantly impact manufacturing companies, particularly in the area of human factors analysis applied to product design and manufacturing process design. The integration of portable multi-modal physiological sensing technologies with subject-specific biomechanical and neurocognitive models implemented within simulation enables sensor and simulation based characterization and prediction of customer and worker performance. This will provide a technique for prevention and mitigation of product usage injuries and workplace injuries as well as enhancing worker performance.

Indirectly, the present invention can also impact companies from a healthcare perspective. Given the occurrence of workplace injuries, in-home rehabilitation will lower employee down time, rehabilitation costs, and increase workplace morale. Additionally, the system described herein has applications in soldier performance enhancement, patient-focused rehabilitation technologies, and assistive robotic devices. Since each of these areas involve modeling, characterization, and simulation and prediction of human biomechanical and cognitive performance, the present invention provides significant impact to these areas.

Finally, while this invention has been described in terms of several embodiments, one of ordinary skill in the art will readily recognize that the invention may have other applications in other environments. It should be noted that many embodiments and implementations are possible. Further, the following claims are in no way intended to limit the scope of the present invention to the specific embodiments described above. In addition, any recitation of "means for" is intended to evoke a means-plus-function reading of an element and a claim, whereas, any elements that do not specifically use the recitation "means for", are not intended to be read as means-plus-function elements, even if the claim otherwise includes the word "means". Further, while particular method steps have been recited in a particular order, the method steps may occur in any desired order and fall within the scope of the present invention.

What is claimed is:

1. A system for patient user-specific rehabilitation, the system comprising:
one or more processors and a non-transitory computer-readable medium having executable instructions encoded thereon such that when executed, the one or more processors perform operations of:
monitoring, using a Mobile Patient Monitor (MPM), sensor data obtained from a plurality of sensors in real-time to generate a quantitative assessment of a physical state and a motivational state of a user;
generating, using a Virtual Patient (VP) unit, predictions related to the user utilizing user-specific biomechanical and neurocognitive models implemented with predictive simulations;
generating rehabilitation guidance using a Virtual Coach (VC) unit through real-time communication with the VP unit;

registering, using an Augmented Reality (AR) unit, video feed of the user with sensor data from the MPM and a set of simulation data from the VP unit; and conveying rehabilitation guidance instructions to the user through dialog-based user-VC interactions; and a lightweight exoskeleton worn by the user configured to convey real-time rehabilitation guidance to the user.

2. The system as set forth in claim 1, wherein the one or more processors further performs an operation of generating at least one biomechanical state prediction with the VP unit using a set of motion and force measurements obtained with the MPM.

3. The system as set forth in claim 1, wherein the one or more processors further performs operations of:
processing the sensor data and a set of user profile data for use as simulation inputs to the VP unit;
generating model-based quantitative assessments of the user's physical state and motivational state using the simulation inputs;
storing the model-based quantitative assessments in a user data archive; and
performing simulations to reveal biomechanical and neurocognitive information related to the user.

4. The system as set forth in claim 1, wherein the one or more processors further perform operations of:
abstracting a set of multi-dimensional time series vectors from the sensor data;
processing, by a Virtual Patient Cognitive Model (VPCM) of the VP unit, the set of multi-dimensional time series vectors;
generating a set of cognitive state estimates from the set of multi-dimensional time series vectors;
determining how the set of cognitive state estimates affect rehabilitation treatment outcomes through processing of the set of cognitive state estimates by the VC unit in order to choose a strategy for desired user results; and
storing a dynamic user profile, comprising the determined effect of the set of cognitive state estimates, in a rehabilitation knowledge base.

5. The system as set forth in claim 1, wherein the one or more processors further performs operations of:
guiding the user, with the VC unit, through rehabilitation treatment by applying a set of rehabilitation knowledge to the user's specific needs through interaction with the VC unit;
generating candidate therapeutic actions using the set of rehabilitation knowledge; and
evaluating, with the user-specific biomechanical and neurocognitive models, likely outcomes if the candidate therapeutic actions are taken.

6. The system as set forth in claim 1, wherein the one or more processors further perform operations of:
generating, with the VP unit, a plurality of simulation feeds related to the user,
wherein a first simulation feed represents a user reference avatar, mirroring the user's motion, and
wherein a second simulation feed represents a user goal avatar, representing motion that the VC unit is guiding the user toward.

7. A computer-implemented method for user-specific rehabilitation, comprising:
an act of causing one or more processors to execute instructions stored on a non-transitory memory such that upon execution, the one or more processors perform operations of:

monitoring, using a Mobile Patient Monitor (MPM), sensor data obtained from a plurality of sensors in real-time to generate a quantitative assessment of a physical state and a motivational state of a user;
generating, using a Virtual Patient (VP) unit, predictions related to the user utilizing user-specific biomechanical and neurocognitive models implemented with predictive simulations;
generating rehabilitation guidance using a Virtual Coach (VC) unit through real-time communication with the VP unit;
registering, using an Augmented Reality (AR) unit, video feed of the user with sensor data from the MPM and a set of simulation data from the VP unit;
conveying rehabilitation guidance instructions to the user through dialog-based user-VC interactions; and
conveying real-time rehabilitation guidance to the user via a lightweight exoskeleton worn by the user.

8. The method as set forth in claim 7, wherein the one or more processors further performs an operation of generating at least one biomechanical state prediction with the VP unit using a set of motion and force measurements obtained with the MPM.

9. The method as set forth in claim 7, wherein the one or more processors further performs operations of:
processing the sensor data and a set of user profile data for use as simulation inputs to the VP unit;
generating model-based quantitative assessments of the user's physical state and motivational state using the simulation inputs;
storing the model-based quantitative assessments in a user data archive; and
performing simulations to reveal biomechanical and neurocognitive information related to the user.

10. The method as set forth in claim 7, wherein the one or more processors further perform operations of:
abstracting a set of multi-dimensional time series vectors from the sensor data;
processing, by a Virtual Patient Cognitive Model (VPCM) of the VP unit, the set of multi-dimensional time series vectors;
generating a set of cognitive state estimates from the set of multi-dimensional time series vectors;
determining how the set of cognitive state estimates affect rehabilitation treatment outcomes through processing of the set of cognitive state estimates by the VC unit in order to choose a strategy for desired user results; and
storing a dynamic user profile, comprising the determined effect of the set of cognitive state estimates, in a rehabilitation knowledge base.

11. The method as set forth in claim 7, wherein the one or more processors further perform operations of:
guiding the user, with the VC unit, through rehabilitation treatment by applying a set of rehabilitation knowledge to the user's specific needs through interaction with the VC unit;
generating candidate therapeutic actions using the set of rehabilitation knowledge; and
evaluating, with the user-specific biomechanical and neurocognitive models, likely outcomes if the candidate therapeutic actions are taken.

12. The method as set forth in claim 7, wherein the one or more processors further perform operations of:
generating, with the VP unit, a plurality of simulation feeds related to the user,
wherein a first simulation feed represents a user reference avatar, mirroring the user's motion, and wherein a second simulation feed represents a patient user goal avatar, representing motion that the VC unit is guiding the user toward.

13. A computer program product for user-specific rehabilitation, the computer program product comprising:
computer-readable instructions stored on a non-transitory computer-readable medium that are executable by a computer having one or more processors for causing the processor to perform operations of:
monitoring, using a Mobile Patient Monitor (MPM), sensor data obtained from a plurality of sensors in real-time to generate a quantitative assessment of a physical state and a motivational state of a user;
generating, using a Virtual Patient (VP) unit, predictions related to the user utilizing user-specific biomechanical and neurocognitive models implemented with predictive simulations;
generating rehabilitation guidance using a Virtual Coach (VC) unit through real-time communication with the VP unit;
registering, using an Augmented Reality (AR) unit, video feed of the user with sensor data from the MPM and a set of simulation data from the VP unit; and
conveying rehabilitation guidance instructions to the user through dialog-based user-VC interactions; and
conveying real-time rehabilitation guidance to the user via a lightweight exoskeleton worn by the user.

14. The computer program product as set forth in claim 13, further comprising instructions for causing the one or more processors to perform an operation of generating at least one biomechanical state prediction with the VP unit using a set of motion and force measurements obtained with the MPM.

15. The computer program product as set forth in claim 13, further comprising instructions for causing the one or more processors to perform operations of:
processing the sensor data and a set of user profile data for use as simulation inputs to the VP unit;
generating model-based quantitative assessments of the user's physical state and motivational state using the simulation inputs;
storing the model-based quantitative assessments in a user data archive; and
performing simulations to reveal biomechanical and neurocognitive information related to the user.

16. The computer program product as set forth in claim 13, further comprising instructions for causing the one or more processors to perform operations of:
abstracting a set of multi-dimensional time series vectors from the sensor data;
processing, by a Virtual Patient Cognitive Model (VPCM) of the VP unit, the set of multi-dimensional time series vectors;
generating a set of cognitive state estimates from the set of multi-dimensional time series vectors;
determining how the set of cognitive state estimates affect rehabilitation treatment outcomes through processing of the set of cognitive state estimates by the VC unit in order to choose a strategy for desired user results; and
storing a dynamic user profile, comprising the determined effect of the set of cognitive state estimates, in a rehabilitation knowledge base.

17. The computer program product as set forth in claim 13, further comprising instructions for causing the one or more processors to perform operations of:
guiding the user, with the VC unit, through rehabilitation treatment by applying a set of rehabilitation knowledge to the user's specific needs through interaction with the VC unit;
generating candidate therapeutic actions using the set of rehabilitation knowledge; and
evaluating, with the user-specific biomechanical and neurocognitive models, likely outcomes if the candidate therapeutic actions are taken.

\* \* \* \* \*